United States Patent [19]

Aszalos et al.

[11] 3,957,754

[45] May 18, 1976

[54] COMPLEXES OF ANTIFUNGAL POLYENE ANTIBIOTICS

[75] Inventors: Adorjan Aszalos, Princeton; John Vandeputte, Milltown, both of N.J.

[73] Assignee: E. R. Squibb & Sons, Inc., Princeton, N.J.

[22] Filed: Jan. 13, 1975

[21] Appl. No.: 540,750

Related U.S. Application Data

[62] Division of Ser. No. 100,492, Dec. 21, 1970, Pat. No. 3,879,374.

[52] U.S. Cl............................ 260/210 AB; 424/180; 424/181
[51] Int. Cl.² .......................................... C07H 15/20
[58] Field of Search .............. 260/210 AB; 424/117, 424/119

[56] References Cited
UNITED STATES PATENTS

2,865,807   12/1958   Dutcher et al. .............. 260/210 AB
3,777,018   12/1973   Gordon et al. ................ 260/210 AB

FOREIGN PATENTS OR APPLICATIONS

795,482   5/1958   United Kingdom .......... 260/210 AB

OTHER PUBLICATIONS

Mazor et al. "Chem. Abst." Vol. 57, 1962, p. 956g.

*Primary Examiner*—Johnnie R. Brown
*Attorney, Agent, or Firm*—Lawrence S. Levinson; Merle J. Smith; Stephen B. Davis

[57] ABSTRACT

Disclosed herein are complexes of polyene antibiotics which are soluble in alcohol or in water and alcohol. These complexes are prepared in alcoholic solutions and have been found to be useful as antifungal agents which can be orally administered.

6 Claims, No Drawings

COMPLEXES OF ANTIFUNGAL POLYENE ANTIBIOTICS

This is a division of Ser. No. 100,492, filed Dec. 21, 1970, now U.S. Pat. No. 3,879,374.

BACKGROUND OF INVENTION

Many complexes of antibacterial agents have been prepared, however, those antimicrobial agents which possess antifungal activity and fall within the polyene series have been difficult to form successfully. The literature shows various attempts to form the salts or complexes of these antimicrobial agents and the difficulty involved therein. Titanium was utilized to complex nystatin in order to make a colorimetric determination of nystatin. This attempt appears in ACTA. PHARM. HUNG., Vol. 32, page 59 (1962), "Examination and Colorimetric Determination of the Titanium (IV) Complex of the Antibiotic Nystatin," by Laszlo Mazor and Maria Papay. In this publication, however, the complex is in fact never separated from the solution. Other attempts to form complexes with a polyene type antibiotic is disclosed in an article appearing in CHEMOTHERAPIA, Vol. 6, pages 326 to 343 (1963), entitled "Biologically Active, Water-soluble Derivatives of Nystatin — Chemical studies," by G. Rapi, P. Cocchi and E. Belgodere. In this article it is clearly stated that the water-soluble derivatives of a polyene macrolide antibiotic is extremely difficult to obtain. However, the article teaches the formulation of a nystatin monohydrochloride which is water soluble but an unstable preparation.

THE INVENTION

The invention relates to a complex of a polyene antibiotic which heretofore was unknown. It is prepared by the reaction of a polyvalent cation with a polyene antibiotic such as nystatin in the presence of an aliphatic alcohol and recovering the desired complex. Complexes of this invention have the formula:

Z-polyene macrolide wherein Z is a polyvalent cation.

As mentioned herein the reactants are reacted in the presence of an alcohol and thereafter the complex of this reaction is precipitated by adding an ether or other nonpolar solvents, such as hexane, benzene, cyclohexane, and so forth, to the reaction solution. The precipitate can then be removed in any convenient manner as by centrifugation, filtering, and the like. The ratio of antibiotic to applied ion is from about 10:1 to about 1:1 to form complexes of the instant invention.

The trivalent cations of this invention are the aluminum, iron, cobalt, chromium, gallium, cerium, tungsten and other halides and nitrates such as aluminum chloride, aluminum bromide, ferric nitrate, cobalt bromide, gallium chloride, cerium iodide, and so forth. The divalent cations of this invention are copper, ferrous, chromium, nickel, zinc and others. Tetravalent ions which may be utilized in the instant invention are stannic and zirconium, such as stannic chloride and zirconium nitrate.

The polyene macrolides are nystatin, pimaricin, rimocidin, amphotericin A, amphotericin B, etruscomycin, lagosin, azacalutin, hamycine, candidin, filipin, fungichromin, pentamycin, flavacid, candicidin, and tylosin.

Alcohols that can be utilized to carry out the reaction are the lower alkyl alcohols of from 1 to 6 carbons such as methanol, ethanol, isopropanol, isobutanol, butanol, heptanol, and so forth. Thus, straight chain and branched alcohols can be utilized in the practice of this invention with superior results being achieved when the alcohol utilized has from 1 to 3 carbons.

Temperatures of the reaction may be maintained at from about ambient to about 50° C., with satisfactory results being obtainable at a temperature of about ambient to 40° C.

The complexes of the trivalent ions of this invention are highly soluble in water which makes them easily formulated for oral or intravenous administration. Prior to the instant invention many of the salts or complexes of polyenes having antifungal activity were not water soluble, therefore, they had to be applied topically. It has been discovered that the complexes of this invention when formulated for oral administration to animals (e.g., dogs cows, pigs, and so forth) yield a high level of the polyene in the blood. Heretofore such results could not be achieved as some of the water soluble salts were unstable and the polyenes per se could not cross into the blood from the digestive system. Utilizing complexes of the instant invention in from between 1,000 to 40,000 units per Kg of weight per day formulations can be prepared in the usual manner, as for example, those described in U.S. Pat. No. 3,491,187.

The following examples are illustrative of the invention. All temperatures are in degrees Centigrade, unless otherwise stated:

EXAMPLE 1

Procedure for Preparing Ferric-Nystatin Complex

Dissolve $FeCl_3.6H_2O$ (273 g.) in methanol (2500 ml.) and add nystatin (2850 g.) to it. Practically all nystatin goes into solution within 5 to 10 minutes. The solution is filtered. The pH of this solution is about 3.4. It is adjusted to about pH of 5.4 with methanolic NaOH.

The ferric-nystatin is precipitated by adding ether or ethylacetate to the above solution. The precipitate is separated by centrifuging and is washed with the precipitating solvent. The compound is vacuum dried and has the following properties:
Soluble in $H_2O$ and alcohols
In vitro activity (S. cerevisiae) equal to nystatin
Iron content 1.8% (wt.)
MW 3000 (ultracentrifuge — pH3 buffer)

EXAMPLE 2

Procedure for Preparing Alumina-Nystatin

The procedure is the same as for Example 1, except that 135 g. aluminum chloride is dissolved in the 2500 ml. MeOH or EtOH and 6650 g. nystatin is added instead of the $FeCl_3.6H_2O$.

The alumina-nystatin formed has the following properties:
Soluble in $H_2O$ and methanol In vitro activity (S. cerevisiae) about equal to nystatin

EXAMPLE 3

Procedure for Preparing Chromium-Nystatin

The procedure is the same as for Example 1 except that 268 g. $CrCl_3.6H_2O$ is mixed into 2500 ml. alcohol and 9550 g. of nystatin is added. Chromium-nystatin has the following properties:
Soluble in $H_2O$ and methanol In vitro activity (S. cerevisiae) about equal to nystatin.

EXAMPLE 4

Cobalt Amphotericin B.

Following the procedures of Example 1 but utilizing 165 g. cobalt chloride in lieu of ferric chloride and 2850 g. amphotericin B in lieu of nystatin, the desired product is recovered.

EXAMPLE 5

Gallium Azacalutin

Utilizing the procedures of Example 1 but substituting 176 g. gallium chloride for ferric chloride and 3000 g. azacalutin in lieu of nystatin, the desired product is recovered.

EXAMPLE 6

Cerium Candidin

Utilizing the procedure of Example 1 but substituting 296 g. cerium chloride for ferric chloride and 2500 g. candidin for amphotericin B, the desired product is recovered.

EXAMPLE 7

Stannic Amphotericin A

Following the procedures of Example 1 but utilizing 438 g. stannic bromide in lieu of ferric chloride and 3900 g. of amphotericin A in lieu of nystatin, the desired product is recovered.

EXAMPLE 8

Procedure for Preparing Ferrous-Nystatin

Dissolve $Fe(NO_3)_2.6H_2O$ (288 g.) in MeOH (2500 ml.) and nystatin (1900 g.) to it. Practically all nystatin goes into solution within 5 to 10 minutes. The solution is filtered. The pH of the solution is about 6.0.

The ferrous-nystatin is precipitated out by adding ether or ethylacetate to the above solution. The precipitate is separated by centrifuging and is washed with the precipitating solvent. The compound is vacuum dried.

Ferrous-nystatin is soluble in methanol.

EXAMPLE 9

Nickel Pimaricin

Utilizing the procedure of Example 1 but substituting 290 g. nickel nitrate for ferric chloride and 2550 g. pimaricin for nystatin, the desired product is recovered.

EXAMPLE 10

Copper Etruscomycin

Utilizing the procedure of Example 1 but substituting 170 g. cuppric chloride for ferrous chloride and 1000 g. etruscomycin for nystatin, the desired product is recovered.

What is claimed is:
1. A complex having the name ferric nystatin.
2. A complex having the name alumina-nystatin.
3. A complex having the name chromium-nystatin.
4. A complex having the name cobalt amphotericin B.
5. A complex having the name stannic amphotericin A.
6. A complex having the name ferrous-nystatin.

* * * * *